United States Patent
Tayebi et al.

(10) Patent No.: US 10,330,624 B2
(45) Date of Patent: *Jun. 25, 2019

(54) METAL OXIDE GAS SENSOR ARRAY DEVICES, SYSTEMS, AND ASSOCIATED METHODS

(71) Applicant: Intel Corporation, Santa Clara, CA (US)

(72) Inventors: Noureddine Tayebi, Menlo Park, CA (US); Xing Su, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 294 days.

This patent is subject to a terminal disclaimer.

(21) Appl. No.: 15/201,437

(22) Filed: Jul. 2, 2016

(65) Prior Publication Data

US 2018/0003660 A1 Jan. 4, 2018

(51) Int. Cl.
*G01N 27/12* (2006.01)
*G01N 33/00* (2006.01)

(52) U.S. Cl.
CPC ....... *G01N 27/124* (2013.01); *G01N 33/0006* (2013.01); *G01N 33/0047* (2013.01); *G01N 27/123* (2013.01); *G01N 27/125* (2013.01)

(58) Field of Classification Search
CPC ...... G01N 27/04; G01N 27/12; G01N 27/123; G01N 27/124; G01N 27/125; G01N 27/14;

(Continued)

(56) References Cited

U.S. PATENT DOCUMENTS 4,457,161 A 7/1984 Iwanaga et al.
4,638,443 A 1/1987 Kaneyasu
(Continued)

FOREIGN PATENT DOCUMENTS

CN 1947007 B 11/2011
EP 2778667 A1 9/2014
(Continued)

OTHER PUBLICATIONS

Barsan et al; Metal oxide-based gas sensor research: How to?; *Sensors and Actuators B Chemical*; Oct. 27, 2006; pp. 18-35; vol. 121; Elsevier.
(Continued)

*Primary Examiner* — Maureen Wallenhorst
(74) *Attorney, Agent, or Firm* — Thorpe North and Western, LLP; David W. Osborne

(57) ABSTRACT

Methods, systems, and devices for detecting an analyte are disclosed and described. In one embodiment, a Metal Oxide Semiconductor (MOS) sensor pixel with a MOS active material is exposed to the analyte in the gas environment. The MOS sensor pixel is heated to a sequence of different predetermined temperatures via a heating element wherein the heating occurs for a period of time for each of the different predetermined temperatures. Response signals are detected, via an electrode, generated by the MOS sensor at each of the different predetermined temperatures. The response signals are assembled into sample data with data features for machine learning. The sample data is compared with data in a standards database. A composition of the analyte is identified based on the data features.

29 Claims, 5 Drawing Sheets

(58) Field of Classification Search
CPC .... G01N 33/20; G01N 33/203; Y10T 436/20; Y10T 436/25875
USPC ........ 436/72, 73, 75, 77, 80, 81, 82, 83, 84, 436/127, 147, 149, 151, 157, 159, 181; 422/82.01, 82.02, 82.12, 83, 88, 90, 98; 73/23.21
See application file for complete search history.

(56) References Cited

U.S. PATENT DOCUMENTS

| | | | |
|---|---|---|---|
| 4,703,646 | A | 11/1987 | Mueller et al. |
| 4,847,783 | A | 7/1989 | Grace |
| 5,019,885 | A | 5/1991 | Yagawara et al. |
| 6,085,576 | A * | 7/2000 | Sunshine ........... G01N 33/0031 340/634 |
| 8,823,396 | B2 | 9/2014 | Astley |
| 9,664,661 | B2 | 5/2017 | Huynh |
| 2002/0142478 | A1* | 10/2002 | Wado ................... G01N 27/124 436/151 |
| 2005/0045477 | A1 | 3/2005 | Wei et al. |
| 2005/0097941 | A1 | 5/2005 | Sandvik et al. |
| 2008/0302672 | A1 | 12/2008 | Sandvik et al. |
| 2014/0260546 | A1 | 9/2014 | Chen |
| 2015/0323510 | A1* | 11/2015 | Huynh ................ H01L 23/3157 73/23.34 |
| 2016/0187279 | A1 | 6/2016 | Noureddine et al. |
| 2017/0284999 | A1* | 10/2017 | Maric .................. G01N 33/497 |

FOREIGN PATENT DOCUMENTS

| | | |
|---|---|---|
| TW | 587165 B | 5/2004 |
| TW | 285801 | 8/2007 |
| WO | WO 2005/073715 A1 | 8/2011 |
| WO | WO 2012/084343 A1 | 6/2012 |

OTHER PUBLICATIONS

Wang et al; Metal Oxide Gas Sensors: Sensitivity and Influencing Factors; *Sensors*; Mar. 15, 2010; pp. 2088-2106; vol. 10; MDPI.

* cited by examiner

METAL OXIDE GAS SENSOR ARRAY DEVICES, SYSTEMS, AND ASSOCIATED METHODS

BACKGROUND

The testing of gases, volatile organic compounds (VOCs), and other airborne substances can be performed for a variety of reasons. One example is personalized health monitoring through breath analysis. Another example is pollution screening and/or monitoring. Yet other examples include environmental screening and/or monitoring, industrial process monitoring, and the like. A variety of sensors can be used to perform such testing to various degrees. Such sensors may vary in size, design, materials, and operation.

DESCRIPTION OF EMBODIMENTS

Figure 1:
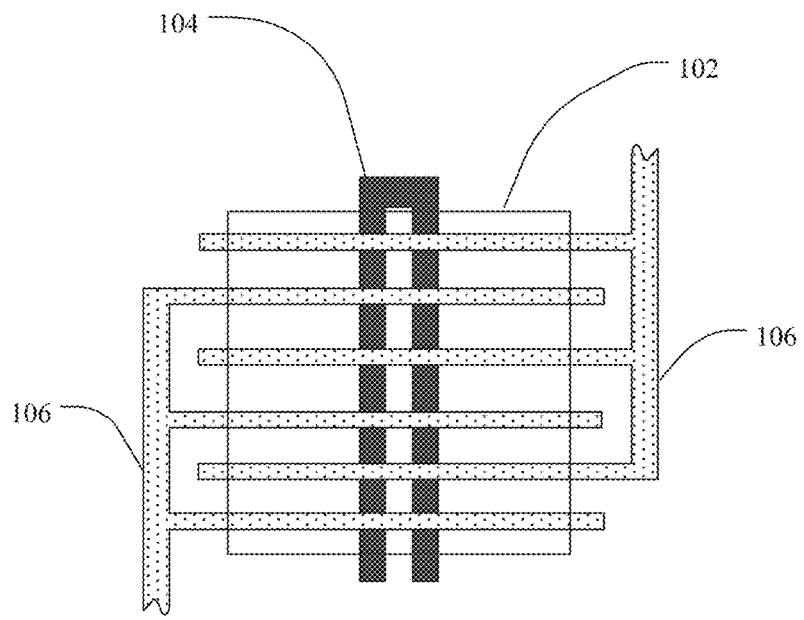
FIG. 1 is a schematic view of a Metal Oxide Semiconductor (MOS) sensor in accordance with an invention embodiment.

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this this written description, the singular forms "a," "an" and "the" include express support for plural referents unless the context clearly dictates otherwise. Thus, for example, reference to "a sensor" includes a plurality of such sensors.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in this written description, like "comprising" or "including," it is understood that direct support should also be afforded to "consisting essentially of" language as well as "consisting of" language as if stated explicitly and vice versa.

"The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in an electrical or nonelectrical manner. Objects or structures described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "analyte" refers to any molecule, compound, substance, agent, material, etc., for which detection is sought. In one aspect, an "analyte" may be capable of detection by a MOS sensor. In another aspect, an "analyte" can be capable of reacting with, and thus creating a detectable change in, a MOS active material. In some circumstances an "analyte" can be present in a gas environment. Non-limiting examples can include gases, airborne inorganic molecules, airborne organic molecules, volatile organic compounds, airborne particulate matter, vapors, vaporized solid or liquid and the like, including combinations thereof.

As used herein, "enhanced," "improved," "performance-enhanced," "upgraded," and the like, when used in connection with the description of a device or process, refers to a characteristic of the device or process that provides measurably better form or function as compared to previously known devices or processes. This applies both to the form and function of individual components in a device or process, as well as to such devices or processes as a whole.

As used herein, "coupled" refers to a relationship of electrical or physical connection or attachment between one item and another item, and includes relationships of either direct or indirect connection or attachment. Any number of items can be coupled, such as materials, components, structures, layers, devices, objects, etc.

As used herein, "directly coupled" refers to a relationship of electrical or physical connection or attachment between one item and another item where the items have at least one point of direct physical contact or otherwise touch one another. For example, when one layer of material is deposited on or against another layer of material, the layers can be said to be directly coupled.

Objects or structures described herein as being "adjacent to" each other may be in physical contact with each other, in close proximity to each other, or in the same general region or area as each other, as appropriate for the context in which the phrase is used.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Example Embodiments

An initial overview of technology embodiments is provided below and specific technology embodiments are then described in further detail. This initial summary is intended to aid readers in understanding the technology more quickly but is not intended to identify key or essential technological features, nor is it intended to limit the scope of the claimed subject matter.

Gas sensors, including VOC sensors, are based on various different principles. For example, a sensor may employ electrochemistry, optical absorption, photo-ionization, enzymatic reaction, metal oxides, resistive-change techniques, and other techniques. Such sensors are typically difficult to miniaturize. For example, electrochemical sensors employ double layer capacitance, which becomes dominant at small scales and impedes sensitivity. Additionally, optical sensors may require bulky components and may have high power requirements. Miniaturized standalone MOS-based gas sensors can have several problems that limit the use of these devices. As one example, due to analyte cross-sensitivity quantitative analysis of an analyte (e.g., measuring concentration) is difficult. While various modifications to MOS sensor designs, such as doping for example, can reduce these problems, analyte cross-sensitivity and consequent lack of selectivity still remains. As another example, changing the operational temperature of a MOS sensor can provide enhanced partial selectivity for a given analyte over a different given analyte. Additionally, environmental conditions can impact the sensitivity of most MOS materials and may lead to erroneous readings due to the lack of proper calibration. One non-limiting example of such an environmental condition is humidity.

Invention aspects relate to devices and systems having a low power, high sensitivity array of MOS sensor pixels that can simultaneously and selectively detect chemical reactions involving one or more analytes and a reactant, such as adsorbed oxygen molecules, at the MOS active materials of the sensor pixels. Such reactions cause changes in the electrical resistance of the MOS active material, thereby providing accurate concentrations of the analyte or analytes. In one aspect, the MOS sensor pixel array is portable and is for use as a field instrument. In another aspect, the MOS sensor array may be used in a laboratory setting. An MOS sensor may be composed of a plurality of components for sensing where each of the components may be referred to as a pixel or sensor pixel. Pixels or sensor pixels may be composed of different MOS active materials within the same array. These various different MOS active materials can be sensitive and/or selective to a specific gas, VOC, or a group of gases and VOCs.

More specifically, in one aspect an array of MOS-based sensor pixels is presented that is selective and can provide single or multiple analyte selectivity including, in some aspects, concentration measurements for single and/or multiple analytes. In one aspect, a MOS pixel is heated to a sequence of different predetermined temperatures via a heating element. The different predetermined temperatures may represent a range of temperatures to which the MOS pixel is heated for a period of time, and includes specific individual temperatures within the time period (e.g. a number of specific temperatures in the range are each achieved and held for a specified time). In some aspects, this may be described as fine-temperature scanning. A response signal is then detected via an electrode. A different response signal may be detected at each of the predetermined temperatures, or other determined increments within the temperature range. The response signals are then assembled into sample data. For example, a data set may comprise more than 5 data points or more than 10 data points. In one example, a data set may comprise from 2 to 400 data points. In one aspect, the sample data set is represented or potentially (virtually) represented graphically by a graph that displays a spectrum of a data set with at least one peak. This may be described as a graphic spectrum. In one embodiment, the data points may be plotted in the spectrum as a function of temperature with a spectrum or profile formed by connecting the data points from one end of the temperature range to the other. It should be appreciated that the sample data is not limited to a graphic spectrum or a spectrum with peaks and may be set of data that is used to extract the features for machine learning and identifying an analyte. The sample data is then compared to standards data in a standards database to identify the analyte. The comparing may include graphic comparison, mathematical de-convolution, statistical analysis, etc. The sample data can also be assembled from multiple identical sensor pixels, each operating at different temperature ranges where the different temperature ranges may be continuous with one another. For example, a first temperature range may be 200-300 degrees (e.g. 200-300 degrees C.) where first MOS sensor pixel for a MOS sensor operates and where a second temperature range is 300-400 (e.g., 300-400 degrees C.) where a second MOS sensor pixel for the same MOS sensor operates simultaneous with the first MOS sensor pixel. Collection of such sample data generated by the first and second sensor pixels operating simultaneously in different temperature ranges can shorten the detection time. The sample data may also be employed to determine a concentration of the analyte. In one aspect, the peak in the spectrum is used to identify the analyte. For example, each unique analyte may have a different peak in a spectrum of data.

Moreover, different MOS active materials can be sensitive to different analytes, as well as have different sensitivities to the same analyte, and can thus be utilized to generate specific analyte selectivities. As such, by utilizing individual MOS sensor pixel heating, different MOS active materials, and/or other techniques for tuning individual MOS sensor pixels, arrays having high selectivity for one or more analytes can be designed and implemented. In one aspect, different pixels or different portions of pixels may be heated to different temperatures, or though different temperature ranges, relative to other pixels within the same array simultaneously. Alternatively, all pixels in an array can be heated to the same temperature or same range of temperatures simultaneously. The different pixels may be composed of the same MOS active material but heated to different temperatures simultaneously in order to detect response signals from the analyte in a more efficient manner. In one aspect, the response signal is based on a change in electrical resistance of a MOS active material (i.e., the sensing layer) as a result of an interaction with an analyte. Once in contact with the analyte, the change in resistance of the MOS film can be detected.

Various MOS sensor designs are contemplated that can be utilized in the implementation of various invention embodiments, and such sensor designs can vary depending on a variety of factors, including the preferences of the designer or user of a given sensing device. The scope of the present disclosure is not limited, therefore, to any specific MOS sensor design.

Generally, a MOS sensor can include a MOS active or sensing material and a heating element to heat the MOS active material to a temperature, or range of temperatures, at which analyte detection is performed. Various additional components can also be included in a MOS sensor, such as temperature sensors, environmental sensors, electrodes, readout circuitry, and the like. A given sensor array can have all MOS sensors of the same design and having the same sensor components, or the sensor array can have different MOS sensor designs and/or components across the array.

One non-limiting example of a MOS sensor is shown in FIG. 1. The sensor can include a MOS active material 102 positioned to be exposed to a sample to be tested. Note that the MOS active material 102 is shown as a transparent layer in FIGS. 1 and 2 to allow the underlying structures to be more clearly shown. A heating element 104 is thermally coupled to the MOS active material 102, and is positioned to facilitate heating of the MOS active material. In some embodiments, heating element geometry may be specifically configured in order to lower or minimize power consumption, lower or minimize heat dissipation, or provide uniform heating. In some embodiments, more than one such advantage can be obtained with a single heating element geometry or configuration. The device can further include one or more electrodes 106 to provide further functionality. For example, in one aspect the electrode 106 can receive and transmit signals generated in the MOS active material. In some cases, a reaction between the MOS active material and an analyte results in a resistance change that can be detected by the electrode. In addition to analyte-related signals (including signals indicating the absence of an analyte), the electrode can receive and transmit signals relating to analyte concentration, the temporal fluctuations in analyte level, as well as signals from other components or modules of the device. Advantageously, in some embodiments, the geometry or configuration of the electrode can be specifically selected to increase or otherwise maximize sensitivity to resistance change in the MOS, and/or to fit a resistance range that is compatible with a readout circuit.

In one aspect, active areas of the MOS sensor, including the sensor pixels, MOS materials, electrodes, etc., are designed on a suspended membrane where the suspended membrane is used to reduce heat dissipation and power consumption. This may be especially useful for portable or wearable application of MOS sensors. In one aspect, the suspended membrane is designed as thin as possible. In one aspect, the power consumption of an MOS sensor is reduced to below one watt (W). In one aspect, the power consumption of an MOS sensor is reduced to below one μW.

Figure 2:
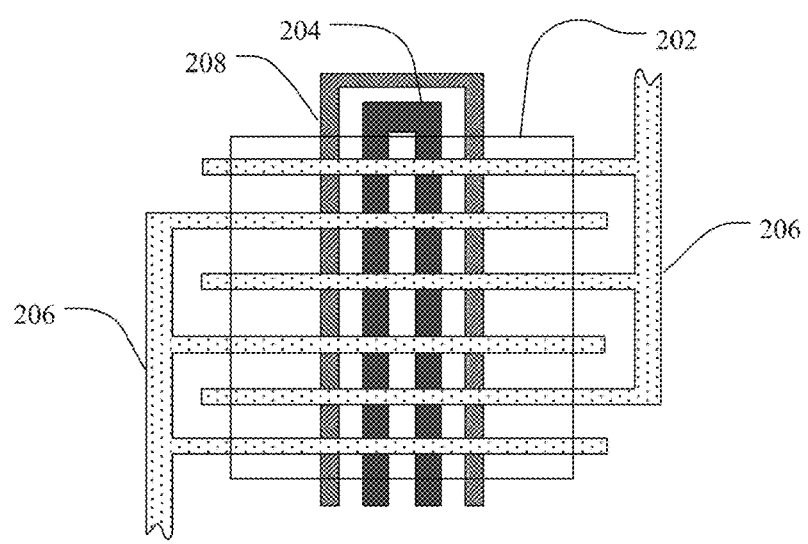
FIG. 2 is a schematic view of a MOS sensor in accordance with an invention embodiment.

FIG. 2 shows another non-limiting example of a MOS sensor including a MOS active material 202 positioned to be exposed to a sample to be tested and a heating element 204 thermally coupled to the MOS active material 202 and positioned to facilitate heating of the MOS active material. The device includes one or more electrodes 206, and a temperature sensor 208 thermally coupled to the MOS active material 202. The temperature sensor can thus detect and/or monitor the temperature of the MOS active material. In some cases, the temperature sensor can detect and report heating conditions generated by the heating element so that the heating of the MOS can be controlled, tuned, or otherwise optimized for a given application. If local temperature were to drift due to thermal fatigue or non-homogeneous dissipation mechanisms (presence of convection and/or radiation), for example, the uniform heating of the MOS active material would be affected, thus disrupting precise and reproducible temperatures. By reading the temperature at the MOS active material and being able to control it precisely, the detection sensitivity of the sensor can be more accurately ascertained, particularly for sensors having a temperature-dependent selectivity to a particular analyte or group of analytes. The temperature sensor can transmit signal to and from the sensor via one or more dedicated electrical channels, or via a shared electrical channel such as the electrode or other electrically useful connection.

In another aspect, a plurality of MOS sensors or sensor pixels is included in an array to provide selectivity to one or more analytes or groups of analytes. Additionally, such an array can provide effective identification and quantification of complex samples of related or unrelated analyte mixtures. For arrays having a size of three or more, MOS sensor pixel arrangements can be in a linear or in a two-dimensional array pattern. A given array can include at least two MOS sensor pixels, where each MOS sensor pixel has the same, similar, or different analyte selectivity as compared to other MOS sensor pixels in the array. In one aspect, a MOS sensor pixel array can selectively detect at least two analytes. In some cases, each of the MOS sensor pixels in an array can be selective to the same or different analytes. In other cases, one or more MOS sensor pixels in an array can be selective to a single given analyte or multiple analytes. As one example, half of the MOS sensor pixels in an array can be selective to one analyte, while the other half of the MOS sensor pixels can be selective to another analyte. In another example, multiple groups of MOS sensor pixels can be included in an array, where each group is selective to a different analyte or group of analytes.

Furthermore, in some cases the individual MOS sensor pixels of an array may not be selective to a specific analyte or analytes, and analyte selectivity of the array is a result of the pattern of partial or cumulative response generated by the array as a whole. In other words, a plurality of MOS sensor pixels can be used as a collective to generate such selectivity. In some embodiments, the individual MOS sensor pixels in the array are not sufficiently selective to distinguish between multiple analytes by themselves. In additional embodiments, the MOS sensor pixels may have differing response characteristics to an analyte in a sample. The differing responses across the MOS sensor pixels in the array can be used as a type of "fingerprint" or pattern to selectively distinguish between analytes that are indistinguishable or difficult to distinguish by the response characteristics of single MOS sensor pixels alone. Once a pattern (e.g. a pattern of data peaks) for an analyte or a mixture of analytes is established, the response of the array to a sample can be compared to that pattern to determine if the analyte or mixture of analytes is present. This pattern recognition process can be used to selectively distinguish a single analyte, a few analytes, as well as complex mixtures of analytes in a sample. While the detection of an analyte or analytes can be dependent on matching a known response pattern or peak to the response of the array, in some cases statistical or other pattern recognition techniques can be employed to selectively detect one or more analytes to which a response pattern is not known. For example, the identity of a mixture of analytes in a sample can be extrapolated from known response patterns of the array to other analytes or mixtures of analytes.

The technique of using fingerprints, peaks, or patterns to selectively distinguish between analytes may rely upon one or more discrete temperature measurements. In one aspect, multiple discrete temperature measurements over a temperature range may generate response signals with spectroscopy-like signatures. For example, fine-temperature scanning of the analyte using the MOS sensor pixels can provide such response signals and related data. Such temperature scanning may be performed at predetermined temperatures. For example, a range of temperatures may be scanned where a given MOS sensor pixel is heated by a heating element to a first temperature for a period of time and is then heated to a second temperature for a period of time. The difference between the first and second temperature may be referred to as an interval, gap, increment, or resolution. Exemplary intervals may be 0.5 1, 5, 10, or 20 degrees Celsius or any other interval. As the intervals are moved closer together, the resultant data becomes more sensitive (not necessarily more sensitive but more informative or selective). In one embodiment, a MOS sensor pixel may scan through an entire range of temperatures sampling data at intervals. The range of temperatures scanned through may be any range of temperatures and may depend upon type of analyte a sensor is designed to identify. In one embodiment, multiple identical MOS sensor pixels may scan through multiple temperature ranges sampling data at intervals, which collectively may scan through an entire temperature range which collectively assemble sampling data for the spectroscopy-like signatures. This is to reduce the detection time. In one embodiment, a sensor may be programmed to change a range of temperatures to be scanned and may also change the period of time each temperature is sampled and may also change the intervals or resolution. In one aspect, a MOS sensor can scan a temperature range of 200 to 400 degrees Celsius. In one aspect, a temperatures range may not exceed an upper temperature where most VOCs will turn into $CO_2$. For example, a MOS sensor may not scan temperatures above 400 or 500 degrees Celsius. In one aspect, after a MOS sensor has identified an analyte, and it has been determined that sampling for such analyte is complete, an MOS sensor pixel may undergo a cleaning cycle to clean the MOS sensor pixel so that it is ready to be exposed to a different analyte. For example, the cleaning cycle may be to heat the MOS sensor pixel to a high temperature such as a temperature exceeding 400 degrees Celsius.

In one aspect, the heating element heats the MOS active material to a sequence of predetermined temperatures. The sequence of predetermined temperatures may be a series of temperatures in a range of temperatures separated by equal or varied intervals. For example, the range of temperatures may be 200-400 degrees Celsius with intervals of 5 degrees so that the predetermined sequence of temperatures is 200, 205, 210, 215, 220 all the way up to 400. In one aspect, the heating element only requires a few milliseconds to heat the MOS sensor pixel to a predetermined temperature. However, the MOS sensor may require a few seconds to generate the response signal at the predetermined temperature. Therefore, the heating element may heat the MOS sensor pixel to a predetermined temperature for a predetermined period of time such as 2-5 seconds. This predetermined period of time can allow the analyte to interact with the MOS active material.

Furthermore, pattern recognition processes can be utilized in an array having analyte-selective MOS sensor pixels. In some cases, for example, a portion of an array can include analyte-selective MOS sensors, and another portion can include analyte-nonselective MOS sensor pixels that utilize pattern recognition for analyte detection. Additionally, in some cases a pattern recognition process can be applied to the response patterns of analyte-selective MOS sensor pixels to detect unknown analytes, analyte mixtures, or analyte mixture concentrations.

Figure 3:
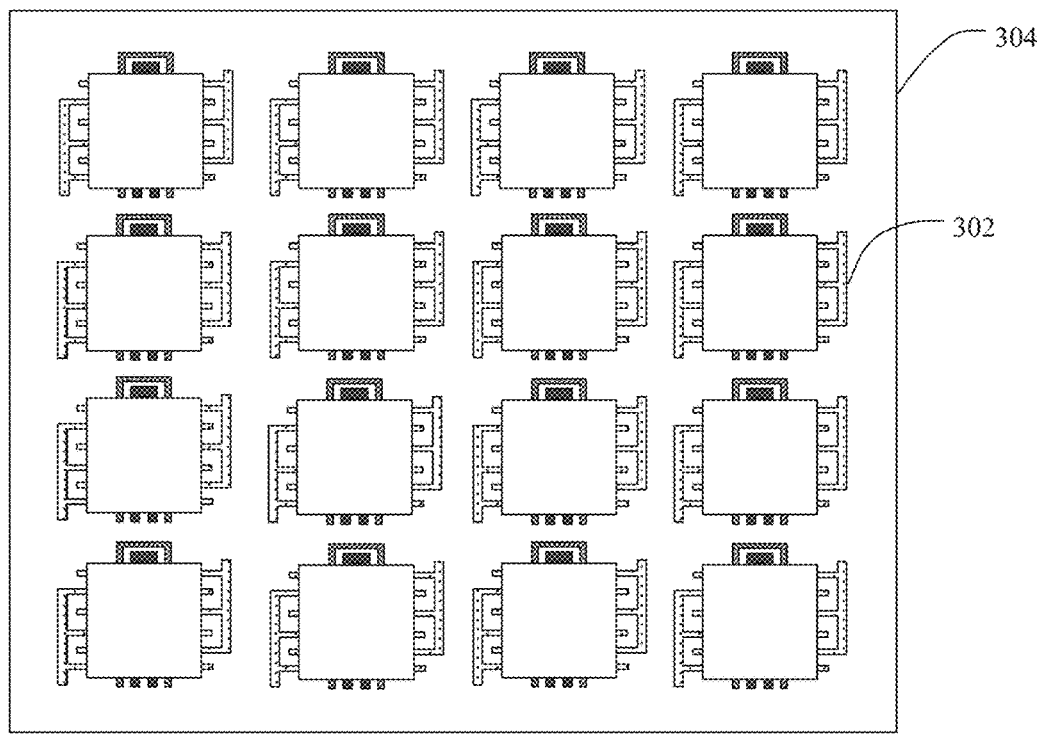
FIG. 3 is a schematic view of a MOS sensor array in accordance with an invention embodiment.

One non-limiting example of a MOS sensor pixel array is shown in FIG. 3, where 16 MOS sensor pixels 302 are arranged into a four-by-four grid on a support substrate 304. It is noted that connections to and from the MOS sensor pixels are not shown. While there is no limit to the number of MOS sensor pixels included in an array, in some aspects the array can include at least four MOS sensor pixels. In other aspects, the array can include at least 16 MOS sensor pixels. In yet other aspects, the array can include at least 24 MOS sensor pixels. In further aspects, the array can include at least 64 MOS sensor pixels. In yet further aspects, the array can include at least 256 MOS sensor pixels. In one aspect, the sensors in the array are co-fabricated with one another. It should be appreciated that the sensors within the array may be each composed of the same MOS active materials or different materials. For example, a portion of the sensors may be composed of a first MOS active material and a different portion of the sensor pixels may be composed of a second MOS active material.

Each MOS sensor pixel in an array can include a MOS active material and a heating element thermally coupled to the MOS active material in a position and orientation to facilitate heating of the MOS active material. One or more temperature sensors can additionally be included in the array. A temperature sensor can be integrated into each MOS sensor pixel as described above, or a temperature sensor can be incorporated at the array level to sense and monitor temperature across a region of multiple MOS sensor pixels. The MOS sensors in the array may be spaced far enough apart so that a given MOS sensor pixel does not cross heat a different MOS sensor pixel. In one aspect, each MOS sensor pixel in the array of sensor pixels is individually controlled and heated to predetermined temperatures.

As has been described, an array can include analyte-selective MOS sensor pixels, analyte-nonspecific MOS sensor pixels, or a combination thereof, including combinations of specific analyte-selective MOS sensors that are selective for the same or different analytes. In the case of analyte-selective MOS sensor pixels, various potential mechanisms can be utilized to generate such selectivity in a sensor. It is noted that any mechanism, characteristic, or property that is capable of tuning a MOS sensor to increase the response selectivity to a given analyte or analytes is considered to be within the present scope. It is additionally noted that the selectivity of a single MOS sensor pixel can include an unambiguous determination of the presence of an analyte, as well as a statistically significant determination. Furthermore, selectivity can additionally be defined based on the intended use of the device. For example, a MOS sensor pixel can be categorized as selectively tuned to an analyte even though there may be cross-selectivity to another analyte that is unlikely to be present in the sample, or that is already known to be present in the sample. For example, a MOS sensor pixel that has cross-selectivity for an analyte of interest and nitrogen can be categorized as selective for that analyte when testing an air sample, provided the response to the analyte is detectable above the response to nitrogen.

Analyte selectivity can be achieved through a variety of mechanisms. In one aspect, the analyte selectivity is achieved by scanning through a range of temperatures at intervals using the MOS sensor pixels. Furthermore, a coating applied to the MOS active material can act as a filter to alter the selectivity of the sensor, such as, for example, a porous polymer coating. Additionally, in some embodiments, the filter need not be a coating on the MOS active material, but can merely be coupled to or otherwise associated with the MOS active material in a fashion that allows the filter to perform its desired function and have a desired effect. For example, filtering can occur by altering the timing at which different analytes reach the MOS active material. In some examples, porous polymers can include without limitation, porous polymer networks with Tetrahedral monomers such as TEPM, TEPA and TBPA. Polytetrafluroethylene (PTFE) can also be used in some embodiments. Additional examples include nanofiber based filtering media, such as a collection of fibers having diameters about 10 nm to about 1000 nm. Nearly any other membrane, resin, or filter structure or material can be used as long as it does not impede the intended function of the sensor device. In a further embodiment, one or more catalysts associated with or within the MOS active material can be used to alter analyte selectivity.

In addition to changes to the active material itself, MOS sensor pixels can also be tuned to be selective to an analyte by adjusting the degree of heating applied to the active material. This differential heating (i.e. multiplexed heating) can be a characteristic designed into each MOS sensor pixel, or it can be a temperature regulation mechanism at the array level. A MOS sensor pixel tuned to heat the active material to an analyte-specific range can include any design element capable of achieving such tuning. Non-limiting examples can include alterations to the heating element material, limiting current to the heating element, alteration of the thickness of material layers between the heating element and the MOS active material, additional materials positioned between the heating element and the MOS active material, and the like, including combinations thereof.

MOS active materials in general can include any metal oxide material that is capable of being used in a sensor to detect an analyte. Non-limiting examples of such materials can include $SnO_2$, $V_2O_5$, $WO_3$, $Cr_{2-x}Ti_xO_3$, $ZnO$, $TeO_2$, $TiO_2$, $CuO$, $CeO_2$, $Al_2O_3$, $ZrO_2$, $V_2O_3$, $Fe_2O_3$, $Mo_2O_3$, $Nd_2O_3$, $La_2O_3$, $Nb_2O_5$, $Ta_2O_5$, $In_2O_3$, $GeO_2$, ITO, and the like, including combinations thereof and various stoichiometric ratios thereof. Thickness of the MOS active material can vary depending on the MOS sensor design and according to the tuning of the sensor, as has been described. Generally, the thickness of the MOS active material should be within the depth of change of the MOS work function but could also be thicker.

Additionally, the MOS active material can be doped, either to affect analyte selectivity or for other functionality of the sensor. Any dopant that is useful in the construction or use of the MOS sensor can be used to dope the active material. Non-limiting examples can include Pt, Pd, W, Au, In, Ru, B, $In_2O_3$ and the like, including combinations thereof. In some cases, a dopant can include any useful catalyst. In other cases, a dopant can include a noble metal. It is noted that, in addition to increasing selectivity, the MOS active material can be doped to decrease selectivity towards an analyte or analytes. In this invention, the MOS active material can be doped MOS or undoped MOS.

The heating element of a MOS sensor can include any type of heat-generating component or structure capable of selectively providing heat to the MOS active material. In one aspect the heating element can be a resistive heating element that includes any type of conductive wire or other structure that can be locally heated by applying a voltage. The heating element can thereby heat the MOS active material to a desired temperature at which analyte detection is performed. Depending on the MOS material used and the analytes being detected, a non-limiting operating temperature range can typically be from about 20° C. to about 600° C. The thickness, material, and/or structural configuration of the heating element can vary, depending on the design of the sensor and the desired analyte selectivity to be achieved. In some aspects, the heat element material can include a dopant to affect the heating properties of the material.

The temperature sensor can include any material or structural configuration that allows sensing and/or monitoring of temperature. In one specific aspect, for example, the temperature sensor can be a conductive wire that changes in resistance with a change in temperature, to thereby allow for accurate temperature monitoring. In some aspects, the heating element and the temperature sensor can be isolated from the MOS active area by an insulating layer. The thickness of the insulating layer can be varied to further affect the heating of the MOS active material.

Additionally, in some cases a feedback element can be coupled to the heating element and the temperature sensor to regulate heating by the heating element. The feedback element can be an electronic component or circuit that can regulate the temperature of the heating element to a set point or range of set points.

The electrode materials can include any material capable of detecting a resistance change or other reaction at the MOS active material, and transmitting a signal indicating that resistance change from the MOS sensor. The electrode can be directly or indirectly connected to the MOS active material, and can include the same or different materials for the detecting and transmitting of the signal. In one non-limiting example, the electrode can be in an interdigitated arrangement, the same or similar to that shown in FIGS. 1 and 2.

The sensitivity of sensor pixel arrays according to aspects of the present disclosure can be affected by a variety of factors. In addition to temperature sensors, MOS sensor pixel arrays can include various sensors to monitor and/or account for such factors. Non-limiting examples of such factors can include sensor effects due to temperature, humidity, aging, non-specific adsorption, flow rate variation, thermo-mechanical degradation, poisoning, and the like, each of which can lead to erroneous detections of analytes. Sensors that monitor one or more of these factors can be used to provide calibration to the array, to indicate needed service of the device, to indicate an inappropriate environment for analyte testing, and the like. Such sensors can be integrated at the MOS sensor level or at the array level, depending on the design of the device. Furthermore, such sensors can be external components integrated at the level of a printed circuit board (PCB) or other system level.

Additionally, one or more environmental sensors can be incorporated into the MOS sensor array or into the MOS sensor device interfaced with the array. An environmental sensor can detect thus at least one environmental condition. While any useful environmental condition is contemplated, in one aspect the environmental sensor can be a humidity sensor. Humidity can affect the sensor reading of the array, and as such, a humidity sensor can be utilized to calibrate the array to a given humidity level. As such, readings in an environment having a level of humidity that can affect the analyte detection and/or analyte concentration can be adjusted to compensate, thus providing much more accurate analyte analysis as compared to non-adjusted readings. Environmental sensors can be integrated at the MOS sensor level or at the array level, depending on the design of the device, or external to the array.

Figure 4:
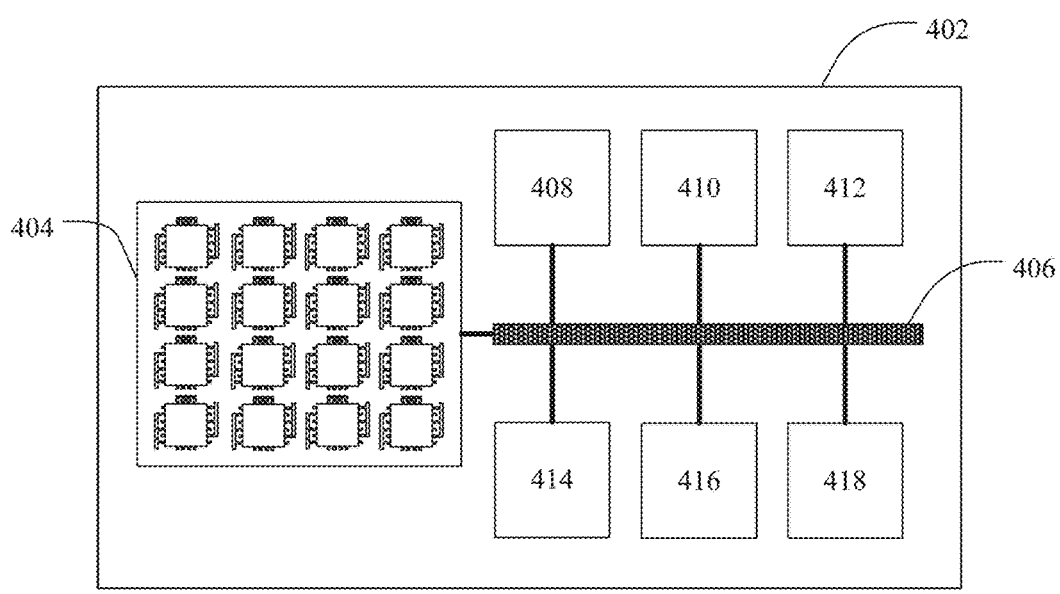
FIG. 4 is a schematic view of an analyte detection system in accordance with an invention embodiment.

An analyte detection system operable to detect a plurality of analytes is shown in FIG. 4. Such a system can include an application specific integrated circuit (ASIC) 402, a transducer or MOS sensor array 404 functionally coupled to the ASIC 402, and an I/O module 406 functionally coupled to the ASIC and the transducer array, which can function to at least provide control and data communication there between. In one aspect, the ASIC and the MOS sensor pixel array can be monolithically integrated. In another aspect, the ASIC and the MOS sensor pixel array can be formed separately and coupled together. The I/O module can be any communication network, communications component, pathway, or connection including, without limitation, an I/O bus or other circuitry. The system may be composed of components that are separate from one another or may be a device where all the components are housed in the same enclosure or housing.

A given analyte detection system can additionally include a heating control module 408, that can be functionally coupled to the I/O module 406, and can operate to control heating of the plurality of heating elements in the MOS sensor pixel array 404. The heating control module may be referred to as a temperature controller and may be capable of controlling heating elements to heat different MOS sensor pixels to different temperatures simultaneously within the same array. Additionally, the heating control module can functionally couple with the temperature sensors, and can thus monitor and/or control the output of the heating elements based on the temperature sensor readings.

Additionally, various modules can be included to address and readout signal from the array. For example, a readout module 410 can be functionally coupled to the I/O module 406, and can operate to read out data from the plurality of MOS sensor pixels in the MOS sensor pixel array 404. In one aspect, the readout module 410 is a display to display the identity and concentration of the analyte. An address module 412 can be functionally coupled to the I/O module 406, and can operate to address the MOS sensor array. The design of a given array, and thus the addressing and readout modules can vary in design and or functionality. For example, the ASIC 402 can be a CMOS ASIC, and therefore the addressing and readout modules can be based on CMOS processing. In other examples, readout can occur similar to a charged coupled device (CCD) readout, a PCB-level readout, or any number of other ASIC or non-ASIC readout and addressing schemes.

MOS sensor pixel array systems can also include various data processing and memory modules. For example, a system can include one or more data or signal processing modules 414 functionally coupled to the I/O module 406. Such processing modules may comprise a processor and can operate to accomplish a variety of tasks, including, without limitation, temperature scanning, comparison of spectrum like data with at least one peak, pattern recognition, pattern extrapolation, concentration or other quantitative analysis, qualitative analysis such as, for example, analyte detection and/or analyte mixture detection, environmental analysis, system status analysis, and the like. It is noted that various functionality can be incorporated into a dedicated module, such as, for example, an environmental analysis module. A data processing module can additionally perform signal processing functions on data received from the readout module, such as, for example, signal amplification and/or filtering. A given processing module function can be accomplished using common or dedicated circuitry and/or processors. For example, pattern recognition can be accomplished using a common circuitry with concentration analysis, or the two processes can have distinct circuitries. One or more nonvolatile memory modules 416 can additionally be included to store a variety of data, including a library, a standards database, calibration information that can be used to compensate for environmental factors, material aging, etc., pattern recognition data, and the like. Various algorithms useful for system control, data manipulation, and/or data analysis can also be resident in a memory module. Non-limiting examples can include matrix transform, genetic algorithms, component correction and principal component analysis, orthogonal signal correction based methods, and the like.

The MOS sensor pixel array system can also include one or more control modules 418 functionally coupled to the I/O module 406. Control modules can operate to control system-level processes such as the heating module, the readout module, etc. Control modules can also operate to control functionality at the array or at the MOS sensor level, such as, for example, monitoring the temperature sensors and controlling the heating elements. In this case, the heating control module is included in the functionality of the control module. Additionally, the control module 418 can accept input and/or programming, thus allowing a user to interact with the system.

Accordingly, in one example signals are detected by the array of MOS sensor pixels and read out by the ASIC or other readout platform, the identities of the various analytes generating the signals are identified, and the concentration of each analyte is determined by the system with a high reliability during the life-time of the sensor array, irrespective of the environmental conditions and aging degradation. The present systems can further include a power supply (not shown).

The MOS devices and sensor arrays of the present disclosure can be fabricated according to any technique or method. For example, such arrays can be made using techniques such as micromachining, MEMS, and microelectronics techniques, printing technologies, chemical synthesis, and the like, including combinations of some or all of these techniques. Furthermore, in cases where an ASIC is used, the MOS sensor array can be integrated with the ASIC either monolithically by post-processing the array directly on the ASIC substrate or in hybrid fashion by fabricating the array separately and using wire-bonding or through-silicon vias (TSVs). In some cases, the ASIC can provide multiplex heating and sensing (MOS resistance change and local temperature), signal amplification, analog to digital conversion and digital output with address based data. It can also include programmable and memory blocks for signal processing, pattern recognition and calibration data for temperature and environmental effect compensations.

As to specific details, the microfabrication of MOS arrays can be performed according to any number of well-known fabrication techniques, and one of ordinary skill in the art would readily be able to fabricate such an array once in possession of the present disclosure.

Figure 5:
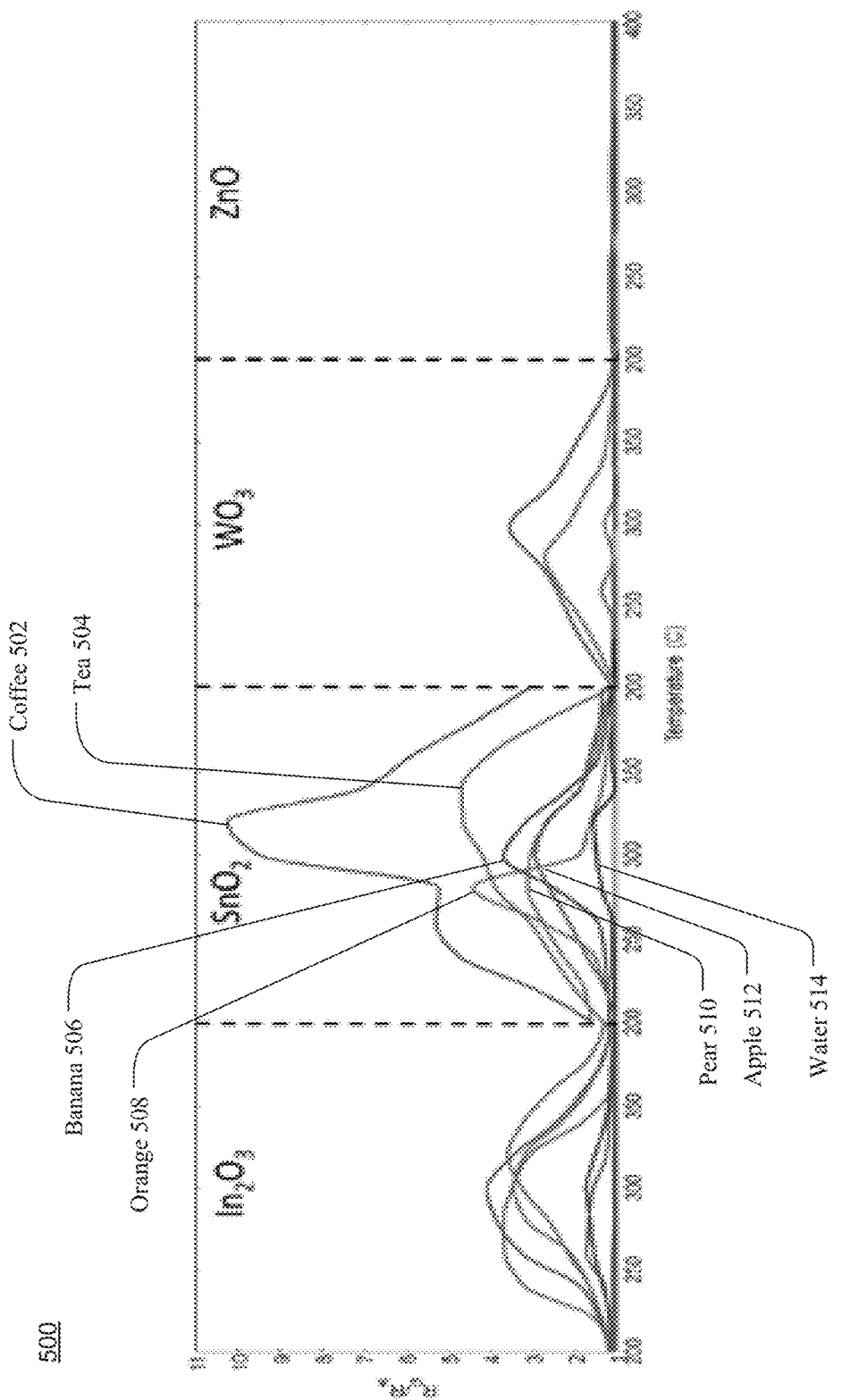
FIG. 5 is a depiction of a graph for determining a composition of analytes in a gas environment in accordance with an invention embodiment.

FIG. 5 depicts graph 500 of sample data of a several different types of analytes exposed to different MOS active materials. Graph 500 depicts four different MOS active materials including $In_2O_3$, $SNO_2$, $ZnO$, and $WO_3$. Each of the four MOS active materials where incorporated into MOS sensors and were exposed to seven analytes. Each of the MOS active materials were then controlled to scan through a range of temperatures between 200-400 degrees Celsius to generate response signals. The response signals were then assembled into the sample data displayed in graph 500. The x-axis of graph 500 represents temperature and the y-axis represents response intensity that is the ratio of measurement reading (resistance of a sensing element in a pixel) over its baseline. Note that the response intensity can be presented differently. As can be seen, the seven different analytes each reacted differently with the four different MOS active materials. For example, the reaction with the ZnO MOS active material was not dramatic and the resulting graph of the sample data for the seven different analytes are not very different from one another. Conversely, the reaction of the analytes with the $SnO_2$ MOS active material produced a graph of sample data where the different analytes are displayed quite differently from one another. Therefore, it may be inferred that $SnO_2$ is a better MOS active material for these analytes compared to ZnO. The graph of the sample data for the seven different analytes for the $SnO_2$ material is labeled identifying each of the analytes. For example, the sample data for the $SnO_2$ material includes, coffee 502, tea 504, banana 506, orange 508, pear 510, apple 512, and water 514. Each of these sample data graphs displays spectrum like behavior where the sample data for each analyte has at least one peak and/or an overall profile through the temperature range. The peak or profile is unique to each unique analyte. Therefore, a library of data or a standards database may be built to identify analytes. The standards database may be stored in a memory associated with the MOS sensor or may be located remotely, such as in the cloud, and accessed by components associated with an MOS sensor. In practice, an MOS sensor pixel may be exposed to an analyte, the MOS sensor pixel then scans through a sequence of predetermined temperatures to generate a response signal. The response signal is then assembled into sample data such as what is depicted in graph 500. The sample data is then compared with a standards database to determine an identity and concentration of the analyte.

In some embodiments, the peak or profile for each specific MOS active agent can be considered in combination with the peak or profile generated by one or more other MOS active agents over the same or different temperature ranges. Such a combination can generate an overall signature or profile that can be compared to the same combination in the standards database. In some embodiments, such processing can provide greater accuracy, sensitivity, or sophistication of analysis.

Figure 6:
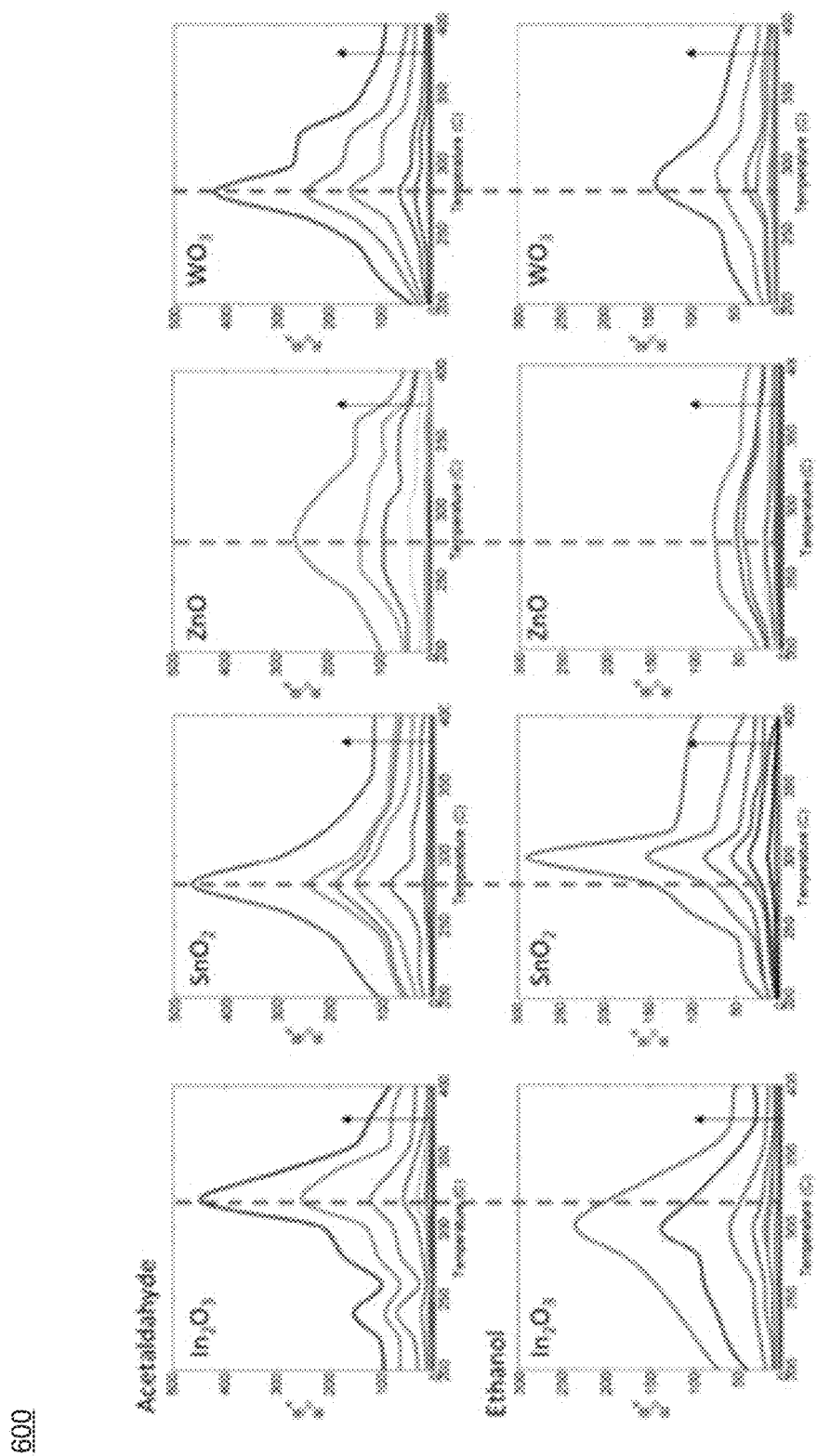
FIG. 6 is a depiction of a graph for building a library used to identify a composition of analytes in a gas environment in accordance with an invention embodiment.

FIG. 6 depicts graph 600 of sample data for two known VOCs exposed to different MOS active materials with different concentrations. Graph 600 depicts sample data that is collected for known VOCs that is then used to build a library of data or a standards database that is then used to later identify corresponding analytes in a known or unknown sample, using MOS sensors, sensor pixels, and methods described herein. The top four graphs of graph 600 depicts sample data for the VOC acetaldehyde collected using four different MOS active materials while the bottom four graphs depict sample data for the VOC ethanol. The four MOS active materials used for testing the acetaldehyde and the ethanol were $In_2O_3$, $SNO_2$, ZnO, and $WO_3$. Each of these four MOS active materials were incorporated into MOS sensors and then exposed to different concentrations of the acetaldehyde and then ethanol. For example, the top left graph shows six spectrum like measurements of sample data. Each of the six spectrum like measurements represents different concentrations of the acetaldehyde exposed to the In$_2$O$_3$ MOS active material. Because these data are used to build the library, the identity of the VOC is known and each of the concentrations were known ahead of the experiment. The sensor pixels with the MOS active materials were each exposed to several different concentrations of the same known VOC. For each exposure, the sensors were made to scan through the range of temperatures 200-400 degrees Celsius at 5 degree intervals for 2 seconds each. The measured response signals were then assembled into the sample data displayed in the graph 500. In each of the eight graphs depicted arrow in the lower right corner indicates concentration increases and the measurement thereof. These concentration measurements are also added to the standards database to determine the concentrations of an unknown analyte while testing an unknown sample. As can be seen, the sample data in each of the eight graphs displays spectrum like behavior where the sample data for each VOC has at least one peak and/or an overall profile. The peak/profile is unique to each unique VOC for each active MOS material over each temperature range.

For a given pair of metal oxide and gas or VOC, the response is also temperature specific. The library or database can be built according to the peaks featured in graph 500 and molecular structures of a set of gases or VOCs given the metal oxide used. Moreover, in the case of multiple gases or VOCs, math models currently used in single processing and optical spectroscopy, can be used to de-convolute the data of measured sample, and gas or VOC species identities, as well as their respective concentration, can be determined according to the database. Such deconvolution would be used to reverse the effects of convolution of the recorded data from the multiple gases or VOCs. In general this may be achieved by finding a solution of a convolution equation such as Equation 1:

$$(f \times g) + e = h$$

where e is a noise emanating from the recorded signal. The deconvolution is usually performed by computing the Fourier transform of the recorded signal h and the transfer function g.

Figure 7:
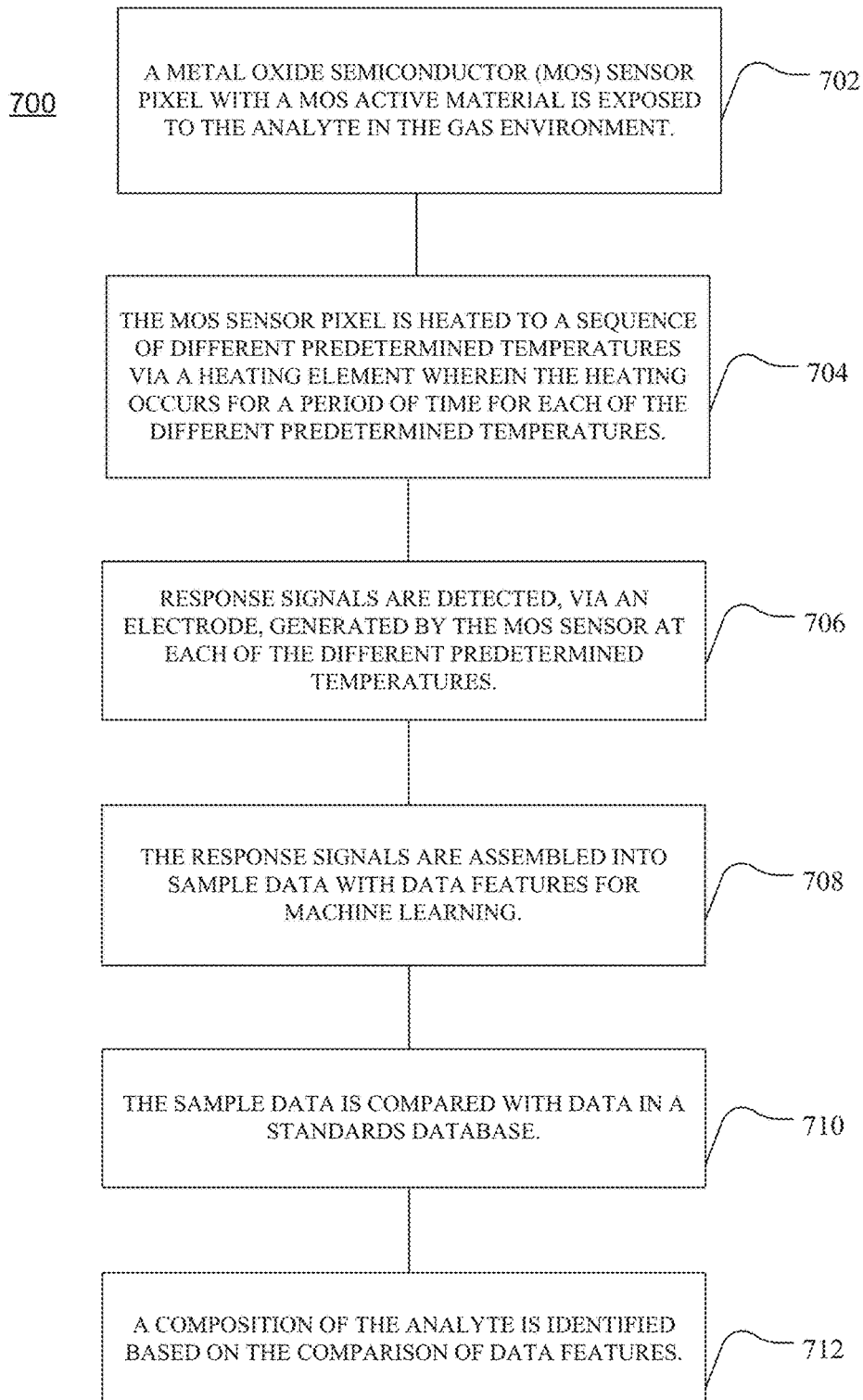
FIG. 7 is a depiction of a method for identifying an analyte in a gas environment in accordance with an invention embodiment.

As is shown in FIG. 7, the present disclosure additionally provides exemplary method 700 for identifying an analyte in a gas environment. Such a method can include exposing a Metal Oxide Semiconductor (MOS) sensor pixel with a MOS active material to the analyte in the gas environment, as in block 702. The method further includes heating the MOS sensor pixel to a sequence of different predetermined temperatures via a heating element wherein the heating occurs for a period of time for each of the different predetermined temperatures, as in block 704. The method further includes, detecting response signals via an electrode, generated by the MOS sensor pixel at each of the different predetermined temperatures, as in block 706. The method further includes, assembling the response signals into sample data with data features for machine learning, as in block 708. The method further includes comparing the sample data with data in a standards database, as in block 710. The method further includes identifying a composition of the analyte based the data features, as in block 712.

EXAMPLES

The following examples pertain to further embodiments.

In one example, there is provided a method of identifying an analyte in a gas environment, comprising:

exposing a Metal Oxide Semiconductor (MOS) sensor pixel with a MOS active material to the analyte in the gas environment;

heating the MOS sensor pixel to a sequence of different predetermined temperatures via a heating element wherein the heating occurs for a period of time for each of the different predetermined temperatures;

detecting response signals, via an electrode, generated by the MOS sensor pixel at each of the different predetermined temperatures;

assembling the response signals into sample data with data features for machine learning;

comparing the sample data with data in a standards database; and identifying a composition of the analyte based on the comparison of the data features.

In one example of a method an array of MOS sensor pixels are employed for detecting the response signal.

In one example of a method each MOS sensor pixel in the array of MOS sensor pixels are heated to different predetermined temperatures simultaneously for the detecting the response signal.

In one example of a method the array of MOS sensor pixels comprises a plurality of individual MOS sensor pixels having different MOS active materials.

In one example of a method the array of MOS sensor pixels comprises at least two individual MOS sensor pixels having different MOS active materials.

In one example of a method the array of MOS sensor pixels comprises from two to ten individual MOS sensor pixels having different MOS active materials.

In one example of a method each individual MOS sensor pixel has a different MOS active material.

In one example of a method the array of MOS sensor pixels comprises four individual MOS sensor pixels having different MOS active materials.

In one example of a method the MOS active material is a member selected from the group consisting of: SnO$_2$, V$_2$O$_5$, WO$_3$, Cr$_2$-xTixO$_3$, ZnO, TeO$_2$, TiO$_2$, CuO, CeO$_2$, Al$_2$O$_3$, ZrO$_2$, V$_2$O$_3$, Fe$_2$O$_3$, Mo$_2$O$_3$, Nd$_2$O$_3$, La$_2$O$_3$, Nb$_2$O$_5$, Ta$_2$O$_5$, In$_2$O$_3$, GeO$_2$, ITO, or combinations thereof.

In one example of a method ein the MOS active material is a member selected from the group consisting of: In$_2$O$_3$, SNO$_2$, ZnO, WO$_3$, or combinations thereof.

In one example of a method the identifying the analyte also identifies a concentration of the analyte based on the comparison of the sample data with the data in the standards database.

In one example of a method the sequence of different temperatures falls within the range of temperatures between 200 degrees Celsius (C) to 400 degrees C.

In one example of a method the sequence of different predetermined temperatures is split among multiple identical MOS sensor pixels.

In one example of a method the sample data is assembled from the multiple identical MOS sensor pixels.

In one example of a method the sequence of different predetermined temperatures are separated by increments of 5 degrees C. or less.

In one example of a method the sequence of different predetermined temperatures are separated by increments of 20 degrees C. or less.

In one example of a method the period of time is a range of time between 0.2 to 20 second, or between 1 to 10 seconds, or two to five seconds.

In one example of a method the analyte is a volatile organic compound (VOC), vapors, vaporized solids, or liquid.

In one example of a method the analyte comprises a plurality of analytes and the identifying identifies each of the plurality of analytes.

In one example of a method the standards database comprises signal data generated by exposing a known analyte to a specific type of MOS sensor pixel, under known conditions.

In one example of a method the database is stored local to the MOS sensor pixel.

In one example of a method the database is stored remote to the MOS sensor pixel.

In one example of a method the database is updated with additional information.

In one example of a method, heating the MOS sensor pixel to a predetermined temperature after the detecting the response signal to clean any remaining analyte from the MOS sensor pixel.

In one example of a method the sample data forms a spectrum with at least one peak and the at least one peak is employed to identify more than one analyte.

In one example of a method the sample data forms a plurality of peaks and the plurality of peaks are employed to identify more than one analyte.

In one example of a method the MOS sensor pixel is doped with a dopant to increase sensitivity and selectivity wherein the dopant is selected from the group of dopants consisting of: Pt, Pd, Si, Ti, or a combination thereof.

In one example of a method a power consumption of the MOS sensor pixel is less than one watt.

In one example, there is provided a transducer array operable to detect an analyte, comprising:
a support substrate;
a plurality of Metal Oxide Semiconductor (MOS) sensor pixels coupled to the substrate, each MOS sensor pixel further comprising a MOS active material configured to be exposed to the analyte;
a plurality of heating elements thermally coupled to the MOS active materials of the plurality of MOS sensor pixels in a position and orientation that facilitates heating of the MOS active materials to a plurality of predetermined different temperatures;
an electrode functionally coupled to the MOS active material and operable to detect response signals from the MOS active material at each of the plurality of predetermined different temperatures; and
a temperature controller having circuitry with logic configured to heat the plurality of heating elements to a sequence of predetermined different temperatures for a predetermined period of time for each of the predetermined different temperatures.

In one example of transducer array the plurality of MOS sensor pixels comprises different MOS sensor composed of different oxides.

In one example of transducer array the analyte is a volatile organic compound (VOC), vapors, vaporized solids, or liquid.

In one example of transducer array the analyte comprises a plurality of analytes and the identifying identifies each of the plurality of analytes.

In one example of transducer array the standards database comprises signal data generated by exposing a known analyte to a specific type of MOS sensor pixel, under known conditions.

In one example of transducer array the database is stored local to the processor.

In one example of transducer array the database is stored remote to the processor.

In one example of transducer array the database is updated with additional information.

In one example of transducer array the sample data forms a plurality of peaks and the plurality of peaks are employed to identify more than one analyte.

In one example of transducer array the temperature controller facilitates simultaneous heating of each of the MOS active materials to a different predetermined temperature.

In one example of transducer array the plurality of MOS sensor pixels comprises at least two individual MOS sensor pixels having different MOS active materials.

In one example of transducer array the plurality of MOS sensor pixels comprises from two to ten individual MOS sensor pixels having different MOS active materials.

In one example of transducer array each individual MOS sensor pixel has a different MOS active material.

In one example of transducer array the plurality of MOS sensor pixels comprises four individual MOS sensors having different MOS active materials.

In one example of transducer array the e MOS active material is a member selected from the group consisting of: $SnO_2$, $V_2O_5$, $WO_3$, $Cr_2-xTixO_3$, $ZnO$, $TeO_2$, $TiO_2$, $CuO$, $CeO_2$, $Al_2O_3$, $ZrO_2$, $V_2O_3$, $Fe_2O_3$, $Mo_2O_3$, $Nd_2O_3$, $La_2O_3$, $Nb_2O_5$, $Ta_2O_5$, $In_2O_3$, $GeO_2$, ITO, or combinations thereof.

In one example of transducer array the MOS active material is a member selected from the group consisting of: $In_2O_3$, $SNO_2$, $ZnO$, $WO_3$, or combinations thereof.

In one example of transducer array the MOS sensor pixel is doped with a dopant to increase sensitivity and selectivity wherein the dopant is selected from the group of dopants consisting of: Pt, Pd, Si, Ti, or a combination thereof.

In one example of transducer array a power consumption of the MOS sensor pixel is less than one watt.

In one example of transducer array the support substrate comprises a suspended membrane to reduce heat dissipation and power consumption.

In one example, there is provided a device operable to identify an analyte, comprising:
a housing comprising:
a transducer array as recited herein;
a support substrate coupled to the plurality of Metal Oxide Semiconductor (MOS) sensor pixels of the transducer array;
the temperature controller with logic configured to:
control the plurality of heating elements to heat the plurality of MOS sensor pixels to a variety of predetermined temperatures wherein the plurality of MOS sensor pixels are heated to each of the predetermined temperatures for a period of time or to simultaneously heat each of the plurality of MOS sensor pixels to a different predetermined temperature;
a processor with logic configured to:
assemble the response signals into sample data with data features for machine learning;
compare the sample data with data in a standards database;
identify a composition of the analyte based on the comparison of the data features; and
a communication component configured to communicate the identity of the analyte to a display.

In one example, there is provided a system operable to identify an analyte, comprising:

a transducer array as recited herein;
a support substrate coupled to the plurality of Metal Oxide Semiconductor (MOS) sensor pixels of the transducer array;
the temperature controller with logic configured to:
control the plurality of heating elements to heat the plurality of MOS sensors to a variety of predetermined temperatures wherein the plurality of MOS sensor pixels are heated to each of the predetermined temperatures for a period of time or to simultaneously heat each of the plurality of MOS sensor pixels to a different predetermined temperature;
a processor with logic configured to:
assemble the response signals into sample data with data features for machine learning;
compare the sample data with data in a standards database;
identify a composition of the analyte based on the data features; and
a communication component configured to communicate the identity of the analyte to a display.

What is claimed is:

1. A method of identifying an analyte in a gas environment, comprising:
exposing a Metal Oxide Semiconductor (MOS) sensor pixel with a MOS active material to the analyte in the gas environment;
heating the MOS sensor pixel to a sequence of different predetermined temperatures via a heating element wherein the heating occurs for a period of time for each of the different predetermined temperatures;
detecting response signals, via an electrode, generated by the MOS sensor pixel at each of the different predetermined temperatures;
assembling the response signals into sample data with data features for machine learning, wherein the sample data forms a spectrum with at least one peak, and the spectrum is a function of the different predetermined temperatures;
comparing the sample data with reference data in a standards database, wherein reference data represents sample data with data features for a plurality of analytes with a known composition; and
identifying a composition of the analyte based on the comparison of the data features of the analyte with the data features of the sample data in the standards database, wherein the at least one peak included in the spectrum formed by the sample data is employed to identify the composition of the analyte.

2. The method as recited in claim 1, wherein an array of MOS sensor pixels are employed for detecting the response signal.

3. The method as recited in claim 2, wherein each MOS sensor pixel in the array of MOS sensor pixels are heated to different predetermined temperatures simultaneously for the detecting the response signal.

4. The method as recited in claim 2, wherein the array of MOS sensor pixels comprises a plurality of individual MOS sensor pixels having different MOS active materials.

5. The method as recited in claim 4, wherein the array of MOS sensor pixels comprises at least two individual MOS sensor pixels having different MOS active materials.

6. The method as recited in claim 5, wherein the array of MOS sensor pixels comprises from two to ten individual MOS sensor pixels having different MOS active materials.

7. The method as recited in claim 4, wherein each individual MOS sensor pixel has a different MOS active material.

8. The method as recited in claim 4, wherein the array of MOS sensor pixels comprises four individual MOS sensor pixels having different MOS active materials.

9. The method as recited in claim 1, wherein the MOS active material is a member selected from the group consisting of: $SnO_2$, $V_2O_5$, $WO_3$, $ZnO$, $TeO_2$, $TiO_2$, $CuO$, $CeO_2$, $Al_2O_3$, $ZrO_2$, $V_2O_3$, $Fe_2O_3$, $Mo_2O_3$, $Nd_2O_3$, $La_2O_3$, $Nb_2O_5$, $Ta_2O_5$, $In_2O_3$, $GeO_2$, ITO, or combinations thereof.

10. The method as recited in claim 1, wherein the MOS active material is a member selected from the group consisting of: $In_2O_3$, $SnO_2$, $ZnO$, $WO_3$, or combinations thereof.

11. The method as recited in claim 1, wherein the identifying the analyte also identifies a concentration of the analyte based on the comparison of the sample data with the data in the standards database.

12. The method as recited in claim 1, wherein the sequence of different temperatures falls within a range of temperatures between 200 degrees Celsius (C) to 400 degrees C.

13. The method as recited in claim 1, wherein the sequence of different predetermined temperatures is split among multiple identical MOS sensor pixels.

14. The method as recited in claim 13, wherein the sample data is assembled from the multiple identical MOS sensor pixels.

15. The method as recited in claim 1, wherein the sequence of different predetermined temperatures are separated by increments of 5 degrees C. or less.

16. The method as recited in claim 1, wherein the sequence of different predetermined temperatures are separated by increments of 20 degrees C. or less.

17. The method as recited in claim 1, wherein the period of time is a range of time between 0.2 to 20 second, or between 1 to 10 seconds, or two to five seconds.

18. The method as recited in claim 1, wherein the analyte is a volatile organic compound (VOC), vapors, or vaporized solids.

19. The method as recited in claim 1, wherein the analyte comprises a plurality of analytes and the identifying identifies each of the plurality of analytes.

20. The method as recited in claim 1, wherein the standards database comprises signal data generated by exposing a known analyte to a specific type of MOS sensor pixel, under known conditions.

21. The method as recited in claim 1, wherein the database is stored local to the MOS sensor pixel.

22. The method as recited in claim 1, wherein the database is stored remote to the MOS sensor pixel.

23. The method as recited in claim 1, wherein the database is updated with sample data with data features for additional analytes with a known composition.

24. The method as recited in claim 1, further comprising:
heating the MOS sensor pixel to a predetermined temperature after the detecting the response signal to clean any remaining analyte from the MOS sensor pixel.

25. The method as recited in claim 1, wherein the sample data forms a plurality of peaks and the plurality of peaks are employed to identify more than one analyte.

26. The method as recited in claim 1, wherein the MOS sensor pixel is doped with a dopant to increase sensitivity and selectivity wherein the dopant is selected from the group of dopants consisting of: Pt, Pd, Si, Ti, or a combination thereof.

27. The method as recited in claim 1, wherein a power consumption of the MOS sensor pixel is less than one watt.

28. A transducer array operable to detect an analyte, comprising:

a support substrate;

a plurality of Metal Oxide Semiconductor (MOS) sensor pixels coupled to the substrate, each MOS sensor pixel further comprising a MOS active material configured to be exposed to the analyte;

a plurality of heating elements thermally coupled to the MOS active materials of the plurality of MOS sensor pixels in a position and orientation that facilitates heating of the MOS active materials to a plurality of predetermined different temperatures;

an electrode functionally coupled to the MOS active material and operable to detect response signals from the MOS active material at each of the plurality of predetermined different temperatures;

a temperature controller having circuitry with logic configured to heat the plurality of heating elements to a sequence of predetermined different temperatures for a predetermined period of time for each of the predetermined different temperatures, wherein the sequence of predetermined different temperatures are separated by increments of 20 degrees C. or less, and a processor configured to assemble the response signals into sample data that forms a spectrum with at least one peak and to identify a composition of the analyte using the at least one peak included in the spectrum, wherein the spectrum is a function of the predetermined different temperatures.

29. The transducer array as recited in claim 28, wherein the plurality of MOS sensor pixels comprises MOS active materials composed of different oxides.

* * * * *